(12) United States Patent
Nord et al.

(10) Patent No.: US 12,369,775 B2
(45) Date of Patent: Jul. 29, 2025

(54) MEDICAL DEVICE

(71) Applicant: MEDEVICE AS, Kragerø (NO)

(72) Inventors: Dag Nord, Oslo (NO); Stephan Andreas Brackmann, Oslo (NO); Lars Petter Waldø-Jensen, Slependen (NP); Arne Røseth, Nesøya (NO); Preben Rene Hjallum, Kragerø (NO); Erik Pavels Petersen, Porsgrunn (NO)

(73) Assignee: MEDEVICE AS, Kragero (NO)

( * ) Notice: Subject to any disclaimer, the term of this patent is extended or adjusted under 35 U.S.C. 154(b) by 412 days.

(21) Appl. No.: 17/632,520

(22) PCT Filed: Sep. 10, 2019

(86) PCT No.: PCT/NO2019/050180
§ 371 (c)(1),
(2) Date: Feb. 3, 2022

(87) PCT Pub. No.: WO2021/049944
PCT Pub. Date: Mar. 18, 2021

(65) Prior Publication Data
US 2022/0273166 A1    Sep. 1, 2022

(51) Int. Cl.
*A61B 1/00*    (2006.01)
(52) U.S. Cl.
CPC .............................. *A61B 1/00133* (2013.01)
(58) Field of Classification Search
CPC ..... A61B 1/00133; A61B 2017/22075; A61M 25/0113
(Continued)

(56) References Cited

U.S. PATENT DOCUMENTS 8,114,032 B2    2/2012    Ferry
9,980,632 B2    5/2018    Banju
(Continued)

FOREIGN PATENT DOCUMENTS

| EP | 1769722 | 4/2007 |
|---|---|---|
| EP | 3155953 | 4/2017 |
| JP | 2003 265406 | 9/2003 |

OTHER PUBLICATIONS

International Search Report Issued in PCT/NO2029/050180, May 20, 2020, pp. 1-3.
(Continued)

*Primary Examiner* — Anh Tuan T Nguyen
*Assistant Examiner* — James Edward Boice
(74) *Attorney, Agent, or Firm* — Jeffrey S. Melcher; Melcher Patent Law PLLC (57) ABSTRACT

It is described an instrument feeder device (201) for use in an endoscope system, for feeding a medical instrument (202) into a body or withdrawing the medical instrument from the body, the instrument feeding device comprising: a connector (302) for connecting the instrument feeding device (201) to a motor 5 (203) for moving the medical instrument (202) through the instrument feeding device (201); a drive wheel (303) arranged to be rotated by the motor, wherein the drive wheel (303) is positioned on one side of the medical instrument (202), an idler wheel (310) positioned on an opposite side of the medical instrument 10 relative the drive wheel (303), a clutch mechanism adapted to push the idler wheel (310) against the medical instrument (202), the clutch mechanism including a rotary button (1012) connected to a spindle (1111), the spindle including a main part and an eccentric part (1111a) which is arranged offset relative a center line through the main part, 15 wherein
(Continued)

the idler wheel is rotatably mounted on said eccentric part of the spindle.

2 Claims, 10 Drawing Sheets

(58) Field of Classification Search
USPC .......................................................... 600/104
See application file for complete search history.

(56) References Cited

U.S. PATENT DOCUMENTS

| | | |
|---|---|---|
| 2007/0078301 A1 | 4/2007 | Kura |
| 2010/0305502 A1 | 12/2010 | Ferry |
| 2014/0277333 A1 | 9/2014 | Lewis |
| 2016/0045709 A1* | 2/2016 | Blacker .................. A61B 34/30 604/95.01 |
| 2018/0153381 A1* | 6/2018 | Wei .................... A61B 1/00087 |

OTHER PUBLICATIONS

Written Opinion Issued in PCT/NO2019/050180, May 20, 2020, pp. 1-5.

* cited by examiner

MEDICAL DEVICE

FIELD OF THE INVENTION

The present invention relates to a device for the insertion and removal of medical devices into the instrument channel of an endoscope.

BACKGROUND

Endoscopy, which includes colonoscopy, gastroscopy and enteroscopy, are medical procedures that are performed to determine if there are any illnesses in the alimentary tract, such as inflammations, infections, premalignant changes, ischemia or tumours. Diagnostic endoscopies are procedures in which the alimentary tract is inspected and tissue (i.e. a biopsy) or fluid (i.e. a cytology) is sampled. The procedure may be performed on either a human or an animal body. Analysis of the tissue or fluid sample allows diagnosis of a condition. For example, diseases such as gastritis, Chrons disease, ulcers and malignancy can be diagnosed. In addition to being used for diagnostic examinations, endoscopic procedures also include therapeutic procedures, such as the removal of polyps, stopping bleedings and the placing of devices (e.g. expandable stents).

Endoscopic procedures are an important tool for medical practitioners and performed by gastroenterologists on a daily basis. The medical instruments that are needed for diagnostic and therapeutic endoscopic procedures are inserted into a body via an instrument channel and pushed along the channel until they reach their intended point of use. It is necessary for the medical practitioner performing the endoscopy to be assisted by someone who holds one end of the medical instrument while the medical practitioner pushes the medical instrument through the channel by holding the other end of the medical instrument. The medical instrument may be 1.2-1.6 meters long and the process of inserting the medical instrument is elaborate and time consuming.

From the patent documents EP17697232 A2 and EP 3155953 A1 there are known endoscope systems including electrically operated drive units for feeding the medical instrument in and out of the instrument channel. Such arrangements may ease the requirement of having an assistant for inserting the medical instrument, but may limit the operational freedom of the medical practitioner in using the instrument.

U.S. Pat. No. 8,114,032 describes a feeding device for an endoscope system, wherein the feeding device is adapted to be connected to a drive motor via a drive shaft. The feeding device includes a number of drive wheels which rotate in response to the rotation of the drive shaft; the feeding device further comprising a clutch mechanism adapted to provide firm contact between the one or more drive wheels and the endoscope cable when engaged. The clutch is engaged with a ratchet mechanism.

SUMMARY OF THE INVENTION

It is an object of the present invention to provide an instrument feeding device for use in an endoscope system, for feeding a medical instrument into a body, wherein the medical practitioner may operate the device without being hampered by the device. Another object is to obtain an instrument feeding device wherein the endoscope system may be easily sterilized. Still another object is to provide a instrument feeding device at a low cost.

Said objects are achieved in an instrument feeding device according to the appended claims.

BRIEF DESCRIPTION OF THE DRAWINGS

Further advantages and features of the invention will appear from the following detailed description and the drawings, wherein.

DETAILED DESCRIPTION

Figure 1:
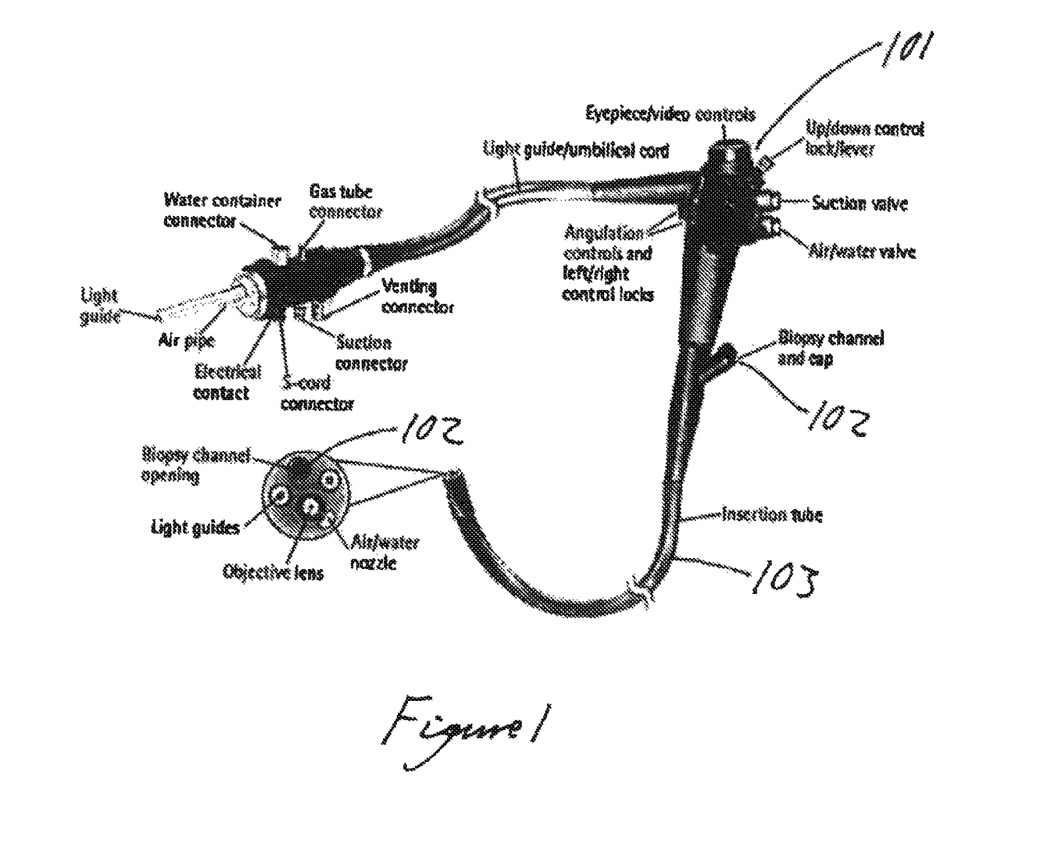
FIG. 1 is a schematic diagram of an endoscope system (prior art)

FIG. 1 shows an endoscope 101 according to prior art. The endoscope 101 may be, for example, a gastroscope or a colonoscope.

An insertion tube 103, which comprises an instrument channel 102 (referred to in FIG. 1 as a biopsy channel), is inserted into the body of a patient. As shown in FIG. 1, a first end of the instrument channel 102 has an opening so that medical instruments can be inserted into the instrument channel 102. A second end of the instrument channel 102, which is at the end of the insertion tube 103 that is inserted into the body, has an opening through which a medical instrument inserted into the first end of the instrument channel 102 can pass through. In use, a medical instrument is inserted into the first end of the instrument channel 102 and passed through the instrument channel 102 until it emerges through the second end of the instrument channel 102. It may then be pushed further into the body until it reaches a point of use for performing a diagnostic or therapeutic procedure.

The medical instrument that is inserted into the instrument channel 102 comprises an instrument part and an elongate part. The instrument part may comprise, for example, scissors for obtaining a sample of tissue. The elongate part comprises one or more wires or tubes and supports the instrument part so that it can be both moved along the channel to a point of use in a body and also operated at the point of use.

The medical instrument may, for example, be any of biopsy forceps, polyp snares, rubber band ligation devices, retrieval baskets as well as other medical instruments. The endoscope 101 may be any flexible endoscopic instrument for providing the passage of a medical instrument into a body. The endoscope 101 is preferably a gastroscope, colonoscope, or enteroscope.

According to known techniques, the medical instrument is inserted into the first end of the instrument channel 102. The insertion is typically performed by the medical practitioner performing the procedure together with an assistant. The medical practitioner manually pushes the medical instrument through the instrument channel 102. The medical instrument may be 1.2-1.6 meters long and the process of inserting the medical instrument is slow. The insertion and removal of the medical instruments also imposes a strain on medical practitioners as the effective length of medical instrument that a medical practitioner may be required to push and pull through instrument channel 102 in a day's work may be 100 m.

Figure 2:
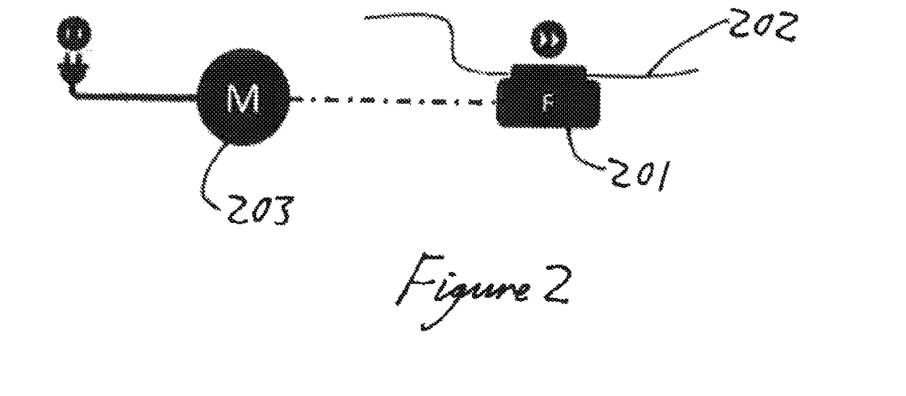
FIG. 2 is a schematic diagram showing how a first embodiment of an instrument feeding device may be incorporated in the system of FIG. 1.

FIG. 2 shows a system according to the present invention comprising an instrument feeding device 201, a motor 203, a drive shaft, an electrical power supply of the motor 203 and a medical instrument 202 that is being passed through the instrument feeding device 201.

The elongate part of the medical instrument 202 is passed through the instrument feeding device 201. The instrument feeding device 201 comprises a number of wheels that contact the medical instrument 202 in the instrument feeding device 201. The rotation of the wheels forces the medical instrument 202 through the instrument feeding device 201. The instrument feeding device 201 also comprises a connector for connecting to an end of the drive shaft. The connector to the drive shaft is physically separated from the wheels in the instrument feeding device 201 such that the connection and use of a non-clean drive shaft does not contaminate a clean medical instrument 202 that is being passed through the instrument feeding device 201, and the passing of a non-clean medical instrument 202 through the instrument feeding device 201 does not contaminate a clean drive shaft. The physical separation of the connector and the wheels may be any configuration that results in the drive shaft and wheels being isolated from each other so that they do not contaminate each other. The instrument feeding device 201 may comprise one or more shields for ensuring that the connected drive shaft and medical instrument 202 do not contaminate each other.

The drive shaft may be any type of shaft or cable capable of transferring the torque of the motor 203 to the instrument feeding device 201. For example, the drive shaft may be a flexible Bowden (speedometer) cable. The drive shaft may alternatively be a non-flexible shaft. The drive shaft may alternatively be replaced by a water turbine or small electric servo engine.

In an alternative embodiment, the motor may integrated in the main endoscope unit. The feeding device may then connect directly to the motor without any intervening drive shaft. In still another embodiment, a motor and battery for powering it may be integrated in the feeding device. The whole unit may then be discarded after use.

The instrument feeding device 201 is configured such that the direction of rotation of the one or more wheels that force the medical instrument 202 through the instrument feeding device 201 is dependent on the direction of rotation of the motor. The operation of the instrument feeding device 201 can therefore be changed from pushing an instrument into a body to pulling the instrument out of a body by reversing the direction of rotation of the motor.

Advantageously, the instrument feeding device 201 is driven by a remote motor 203. The instrument feeding device 201 does not comprise a motor 203 and this reduces the cost of the instrument feeding device 201.

After the use of an instrument feeding device 201, the instrument feeding device 201 can be disconnected from the motor/drive shaft and disposed of. A new instrument feeding device 201 can be connected to the same motor/drive shaft and another biopsy operation quickly and easily performed.

Figure 3:
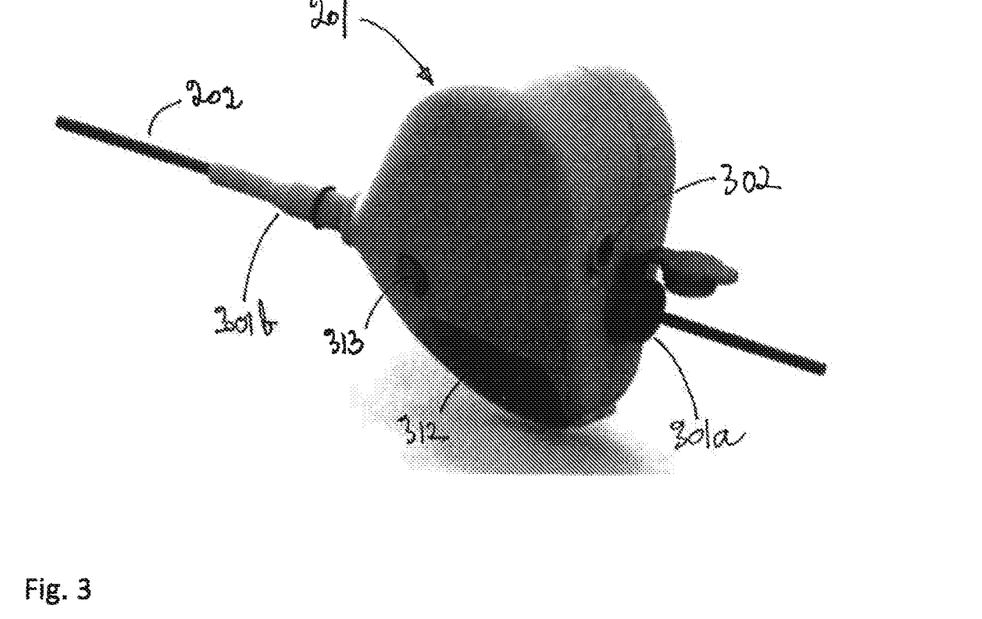
FIG. 3 is an external view of the feeding device.

FIG. 3 is an external view of the inventive instrument feeding device. The device includes an outer housing with an input port 301a for the medical instrument and an output port 301b forming an instrument channel insert plug. Further, there is a contact 302 for connecting the drive shaft or Bowden cable from the external motor 203, or for contacting the motor directly, a push button 312 for operating an internal clutch mechanism for engaging the instrument feeding device 201 to the medical instrument 202, and a release button 313 for releasing the engagement between the feeding device and the medical instrument. In the embodiment shown in the figure, the contact 302 is of the hexagonal type. However, any type of suitable contact may be used, e.g. of the spline type, a blade type contact, etc. When using the endoscope system, the feeding device 201 is connected to the endoscope system by plugging the insert plug 301b into the endoscope system. A particularly preferred point if attachment to the endoscope 101 is at the end of the instrument channel 102. The attachment ensures that the instrument feeding device 201 effectively remains stationary while the medical instrument 202 moves through it. Alternatively, the instrument feeding device 201 may be held by the medical practitioner. The medical instrument is then threaded through the feeding device. The push button is depressed for engaging the drive mechanism in the feeding device to the medical device. The external drive unit may then be activated, e.g. with a foot pedal, i.e. switch, for feeding the medical instrument into instrument channel of the endoscope system. The medical instrument is fed into the instrument channel until about 5 cm from the end of the channel. When the instrument is positioned in the desired location near the end of the instrument channel, the release button is depressed releasing the engagement between the feeding device and the medical instrument. Then, the medical practitioner may operate the medical instrument fully independent of the feeding device and feed it further into the body of the patient manually. This is a safety measure, to ascertain that the medical device does not harm the patient.

Figure 4:
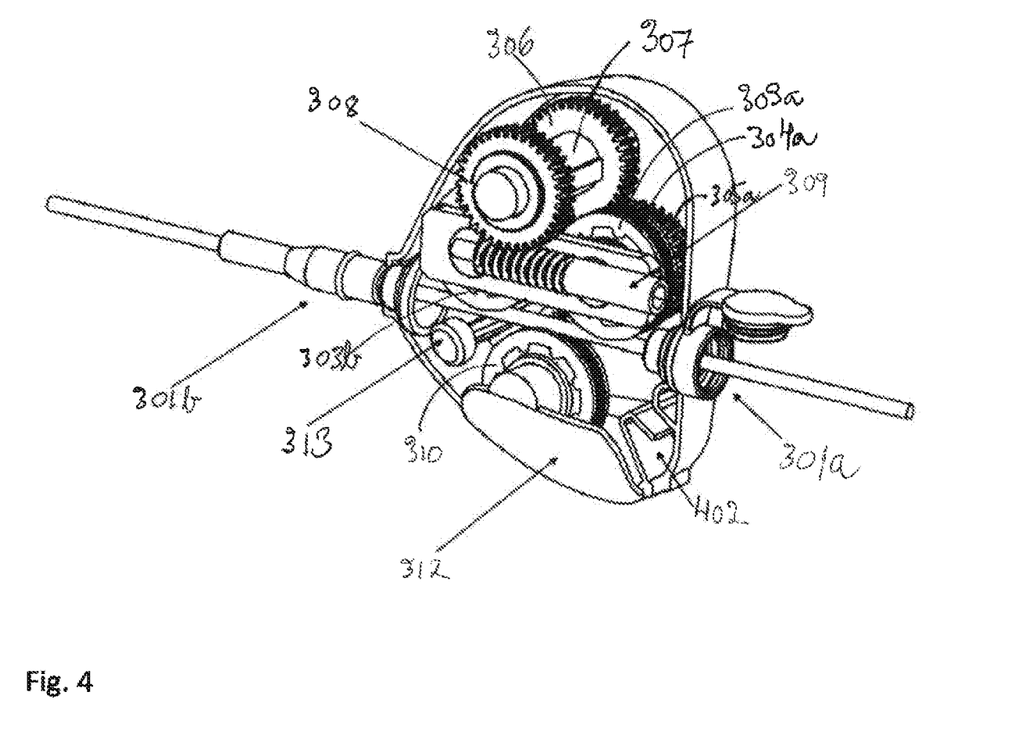
FIG. 4 shows the internal workings of the feeding device.

FIG. 4 shows the inner parts of the instrument feeding device 201. The instrument feeding device includes a housing with two ports 301a, 301b on opposite sides thereof through which the medical instrument 202 passes. The medical instrument 202 may pass in both directions through the instrument feeding device 201. The drive mechanism moving the medical instrument through the instrument feeding device preferably includes two upper drive wheels 303a and 303b inside the encapsulation, each drive wheel being adapted to contact the medical instrument 202.

The drive wheels have a solid core part and an outer part that is made of a soft material, such as rubber. The solid core part may be made in plastic and the soft outer part moulded onto this to secure a firm connection between the two parts avoiding any slip there between. The soft outer part of each wheel provides for good frictional contact with the medical instrument which is necessary for moving the instrument. However, the rubber outer part on each wheel should have an appropriate thickness. This means that the rubber part should not be so thick that the medical instrument is completely embedded in or surrounded by rubber when the drive and idler wheels are closed together preventing the hard inner cores from exerting sufficient pressure and grip on the medical instrument.

The circumference of the wheels may also be patterned as shown (herringbone or tractor pattern) for further increasing the friction between wheels and medical instrument, as the medical instrument may be quite slippery.

Each drive wheel is connected to a respective cog wheel 305a, 304a. Each drive wheel and associated cog wheel may of course be made as a single unit. The cog wheels 305a, 304a are in mesh with a common transfer cog wheel 306 which may be connected to a worm gear 308, 309 through a short axle 307. The worm gear includes a gear cog wheel 308 in mesh with a worm screw 309. An end of the worm screw is projecting trough the encapsulation and terminated in the contact 302 for engagement with the drive shaft providing rotational power from the external motor 203.

This is the mechanism that drives the medical instrument forward and back. However, to provide a proper engagement between the drive wheels 303a, b in the drive mechanism and the medical instrument 202, the instrument feeding device 201 is equipped with a clutch mechanism. The clutch mechanism includes an idler wheel 310 which may be pressed against the underside of the medical instrument 202 pressing this towards the two drive wheels 303a, b above. The idler wheel 310 may also be provided with a soft outer part 311. The idler wheel may be pressed towards the medical device with a push button 312, and there is a ratchet mechanism adapted to hold the idler wheel in the engaged position. There is also a release button 313 for disengaging the ratchet mechanism and thus release the engagement of the wheels. In this way, this arrangement works as a clutch allowing the instrument feeding device to move the medical instrument for positioning it, and then to release the engagement between device and instrument providing full freedom for the medical practitioner to operate the instrument.

The worm gear shown in FIG. 4 may be advantageous in that it may have a braking function preventing the medical instrument from possibly forcing its way back through the feeding device when the device is inactivated. However, the worm gear may also be dispensed with and the drive cable or motor connected directly to one of the wheels through a suitable contact at the side of the enclosure. The motor must be able to drive the feeding device at a suitable rotation rate, and may therefore include a gear mechanism.

This embodiment with two drive wheels and a single idler wheel facing the drive wheels is advantageous in that the medical instrument will bend slightly when passing the wheels. This will increase the contact surface and increase the friction between wheels and instrument. However, alternative embodiments may be contemplated, such as an opposite configuration with a single drive wheel and two idler wheels, or a configuration with a single drive wheel and a single idler wheel opposing the drive wheel, or two drive wheels and two idler wheels, each idler wheel directly facing a drive wheel.

Figure 5:
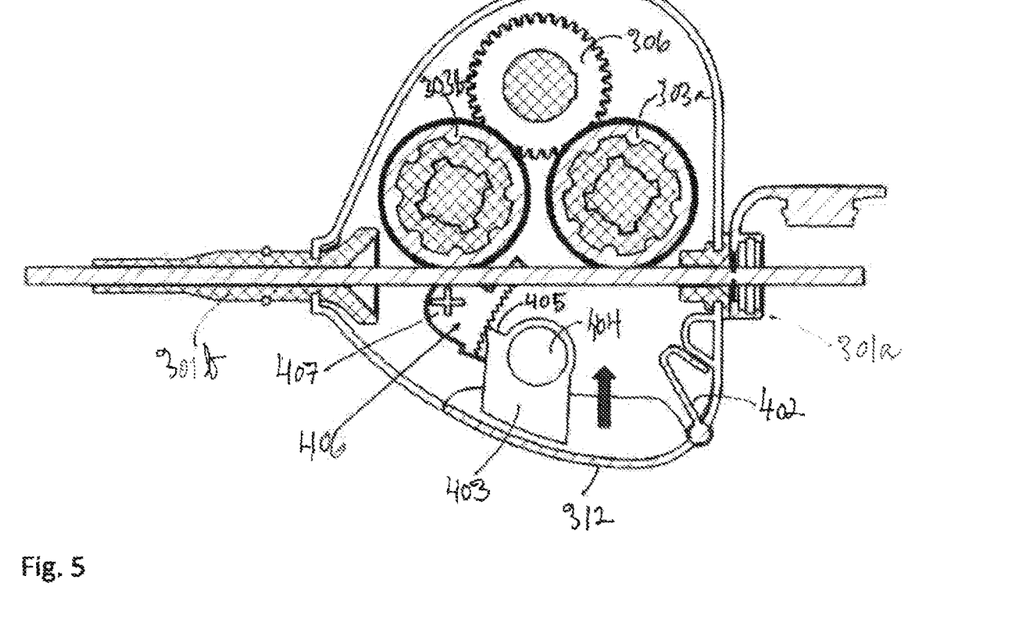
FIG. 5 is a partial section through the feeding device, FIG. 6a, b shows another embodiment of the invention.

FIG. 5 is a section view through the instrument feeding device according to FIG. 4. The worm gear and idler wheel have been removed to show the ratchet mechanism holding the idler wheel towards the medical instrument. The mechanism includes a push button 312 flush with the enclosure wall. The button includes a hinge shaft 404, a spring part 402 and a projecting ratchet part 406. The push button is hinged to the enclosure wall in hinge shaft 404 at one end of the push button. The spring part 402 is projecting from the hinge shaft urging the push button towards the position shown in FIG. 5. Further, the mechanism includes a key 403. The key 403 includes a point 405 engaging the toothed path of the ratchet part 406. When the push button is depressed, the idler wheel will be pressed against the medical instrument pressing this further against the drive wheels. Simultaneously, the key will slide along the toothed part, become locked to the ratchet part, and thus prevent the idler wheel from returning when the operator releases the pressure on the push button. In this position the operator may operate the motor, e.g. using a foot pedal, to position the medical instrument. When the instrument has been properly positioned, the clutch mechanism may be released. This is done by depressing the release button 313. This button is not shown on the figure, but is mounted on the cross-shaped projection 407. By depressing the button, the ratchet part will be bent out of engagement with the key. Then the push button with idler wheel and key will snap into its initial position and release the grip on the medical instrument.

An important requirement is that the medical instrument is initially clean when inserted into a body. When feeding a clean medical instrument into a body, all parts of the instrument feeding device that contact the medical instrument must also be clean otherwise the contact will result in the medical instrument losing its clean property, i.e. the medical instrument will be contaminated. Thus, at the start of the endoscope procedure all parts involved must clean or clean. When the procedure is finished, the both the medical instrument and the feeding device will be contaminated. The instrument may be cleaned. However, to subsequently clean the non-clean instrument feeding device is difficult and expensive.

To avoid this problem, the inventive instrument feeding device is preferably a single use device. The instrument feeding device is provided to its point of use in a clean condition having never been used before. After use, the instrument feeding device is typically discarded and an unused clean instrument feeding device is used for the next endoscopic procedure. Advantageously, it is not necessary to sterilise each instrument feeding device after its use.

As each instrument feeding device is disposed after a single use, it is preferable for the manufacturing cost of the instrument feeding device to be low. Accordingly, the instrument feeding devices according to embodiments preferably consists of low cost components.

Figure 6A:
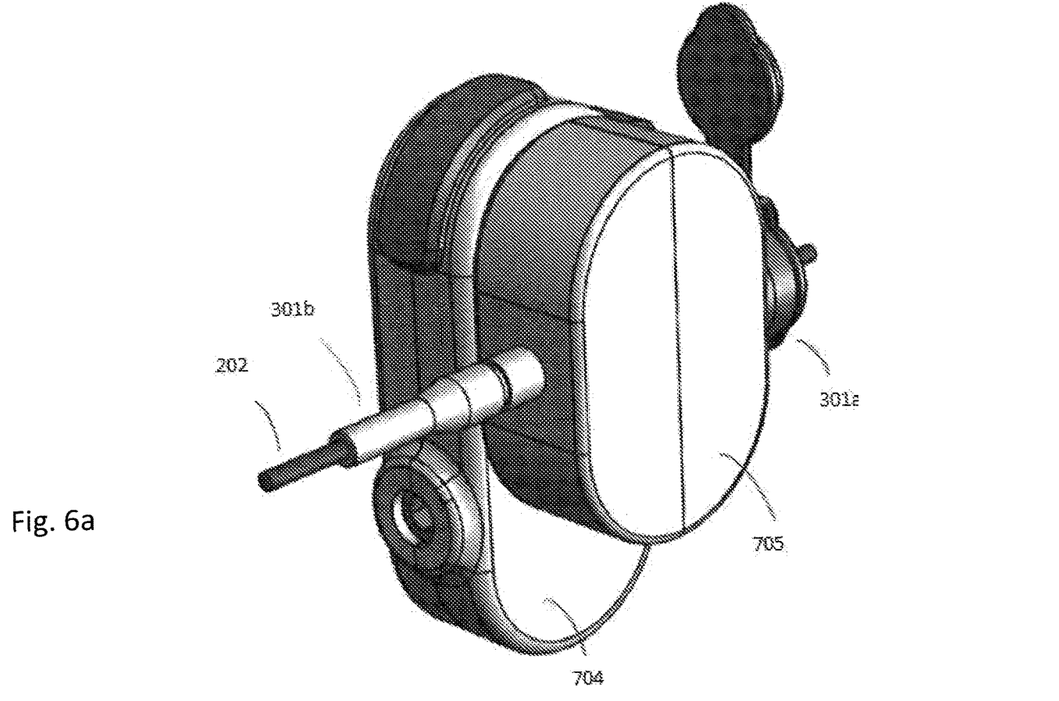
Figure 6B:
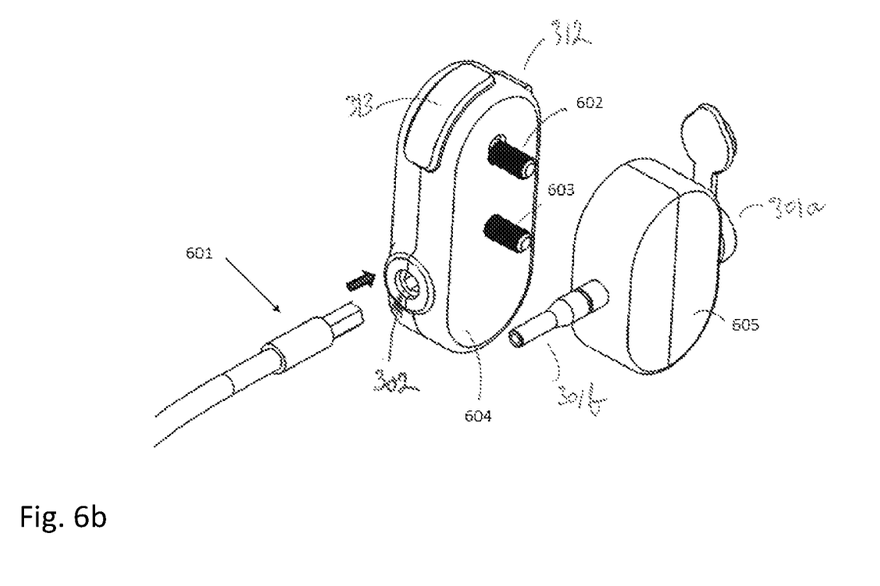

FIG. 6a shows an embodiment of the invention designed to lower the costs of the system. For this end the instrument feeder device includes two parts, namely a gear part 604 and a separate feeder cassette 605. Only the feeder cassette is disposed after each examination cycle. The gear part 604 includes the drive mechanism and the clutch mechanism with push button 313 and release button 312. Drive is delivered via the drive cable 601 (or another shaft from the motor) and transferred to the feeder cassette 605 via two output shafts 602 and 603. The cassette includes input and output ports 301a, b for accepting the medical instrument and the drive wheels for feeding the instrument there through. FIG. 6b shows the cassette mounted onto the gear part.

Figure 7:
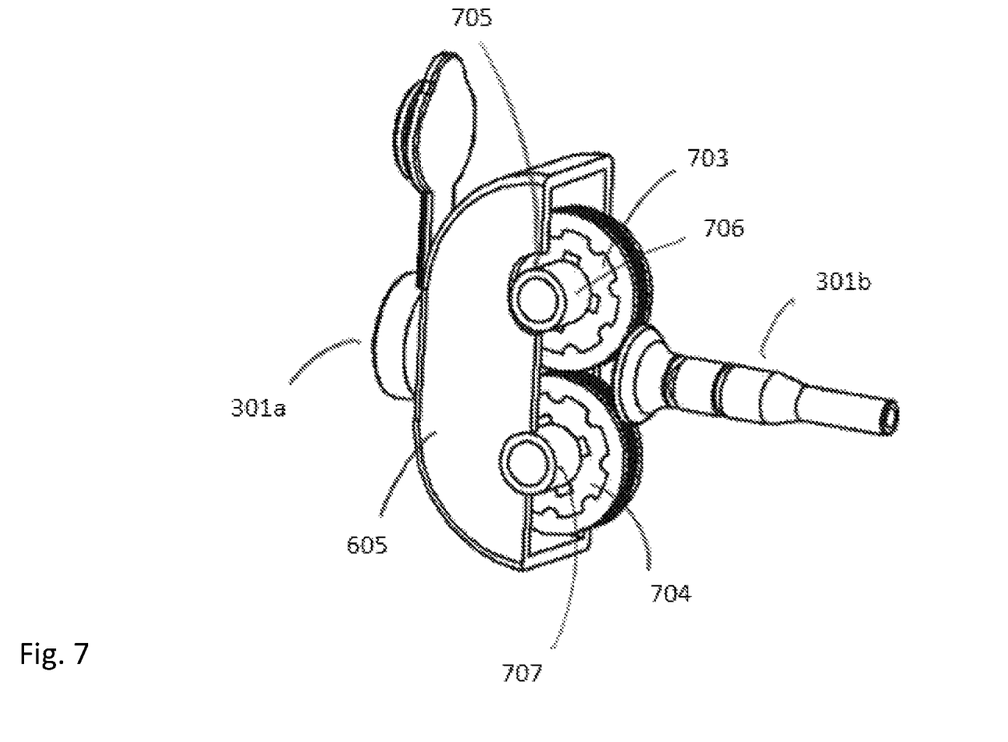
FIG. 7 is a schematic view of a component included in the embodiment shown in FIG. 6.

FIG. 7 shows the internal components of the feeder cassette. This embodiment uses only one drive wheel 704 and one idler wheel 703, of the same construction as in the previous embodiment, each with an axle 707 and 706 adapted to engage the output shafts 602 and 603. The upper axle is supported in oval holes 705 at each end allowing the idler wheel to be moved along the hole.

Figure 8A:
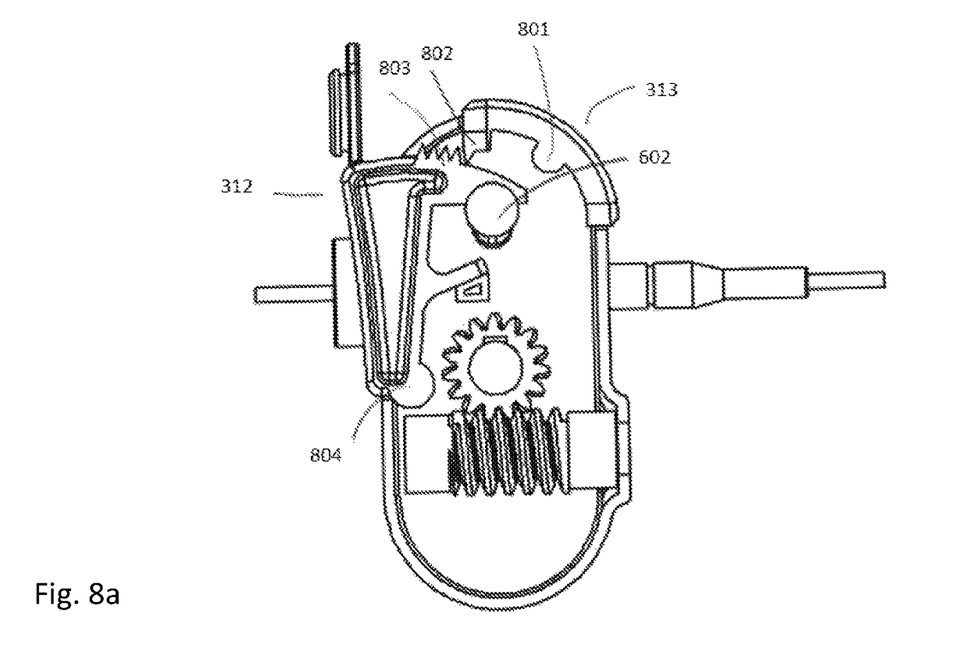
FIG. 8a-c shows another component of this embodiment, and FIG. 9a, b shows a detail of the component shown in FIG. 8.

FIG. 8a is a cross section through the gear part, with the upper axle in its upper position, which means that the feeder cassette will not engage the medical instrument. The push button 312 includes a projecting part engaging a slot in the upper output shaft 602. The release button 313 includes a key 802 adapted to engage the ratchet 803 in the projecting part of the push button 312.

Figure 8B:
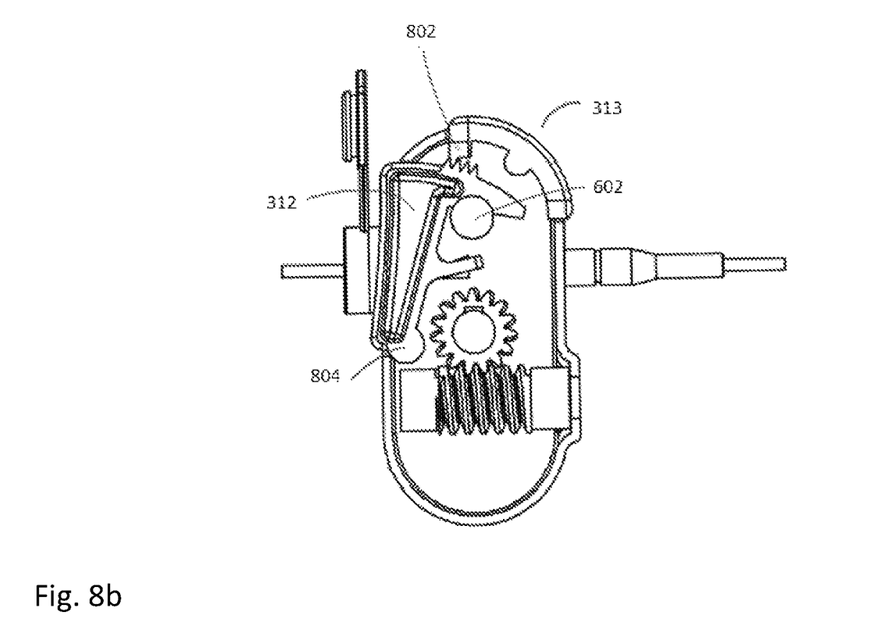

FIG. 8b shows the gear part with the push button 312 depressed. The button is hinged to the encapsulation in the hinge 804 and projecting part will force the upper shaft 602 downwards, while the key 802 engages the ratchet and locks the push button in its depressed position.

Figure 8C:
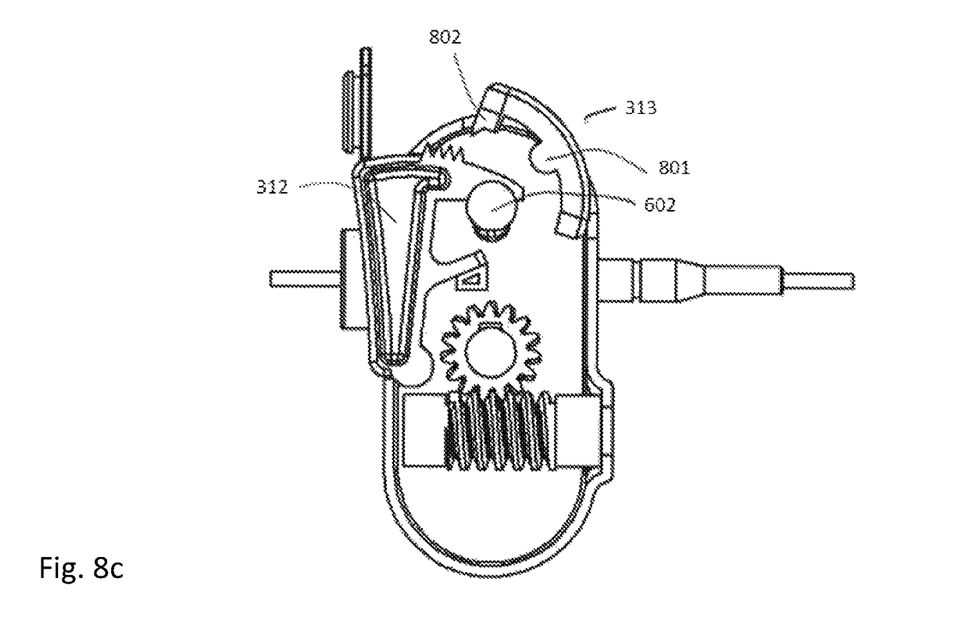

In FIG. 8c the release button 313 is depressed removing the key 802 from its engagement with the ratchet, as the release button is hinged to the encapsulation in the hinge 801. The upper shaft 602 has then returned to its initial position.

Figure 9A:
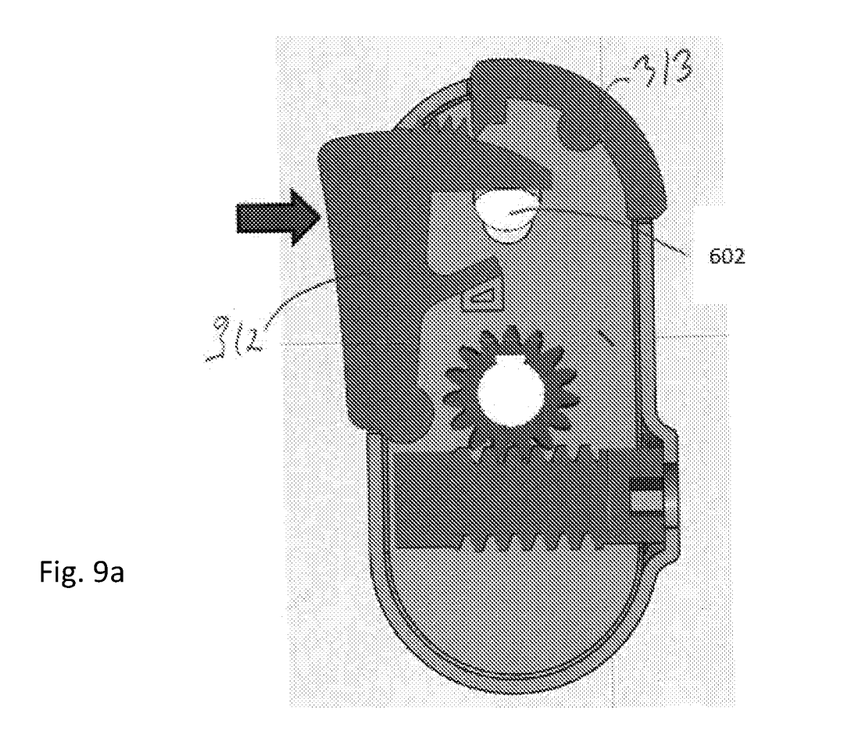
Figure 9B:
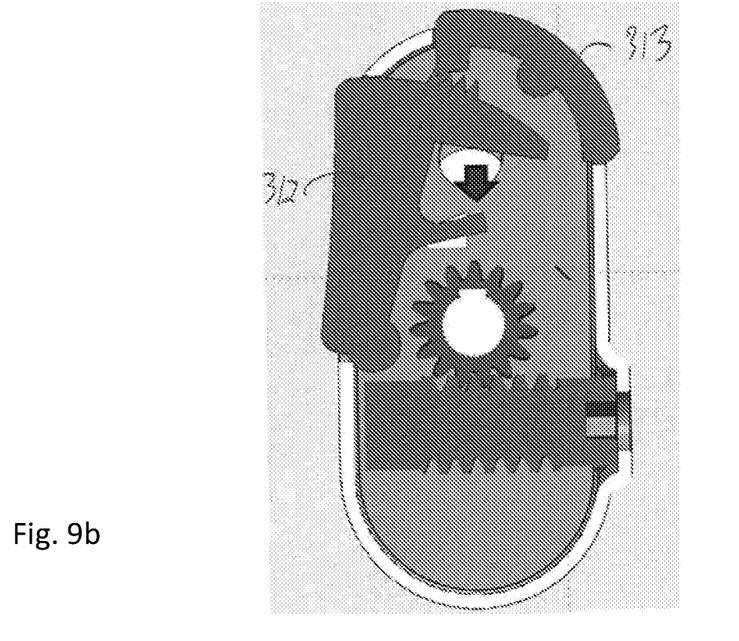

FIG. 9a, b shows how the push button 312 is engaging the upper shaft 602 entering a slot in the shaft.

However, also versions with two drive wheels and one or two idler wheels may be designed using a separate feeder cassette.

During the development of the new feeding device it has been found that the embodiments shown in FIGS. 2-9 have some strong and weak points. First, the soft drive wheels with their patterned outer layer provide sufficient grip on the instrument cable to allow dispensing with the three wheel design, i.e. that a single drive wheel arranged directly opposite an idler wheel will provide enough traction power to the medical device. Only in special circumstances it may be needed to use two drive wheels and one idler wheel, or the opposite configuration with two idler wheels and a single drive wheel. Another alternative is to use two drive wheels and two idler wheels in such circumstances. Secondly, the ratchet mechanism for the clutch has proven not to be sufficiently reliable. Thus, a third embodiment of the feeding device has been developed, as illustrated in FIGS. 10-15.

Figure 10:
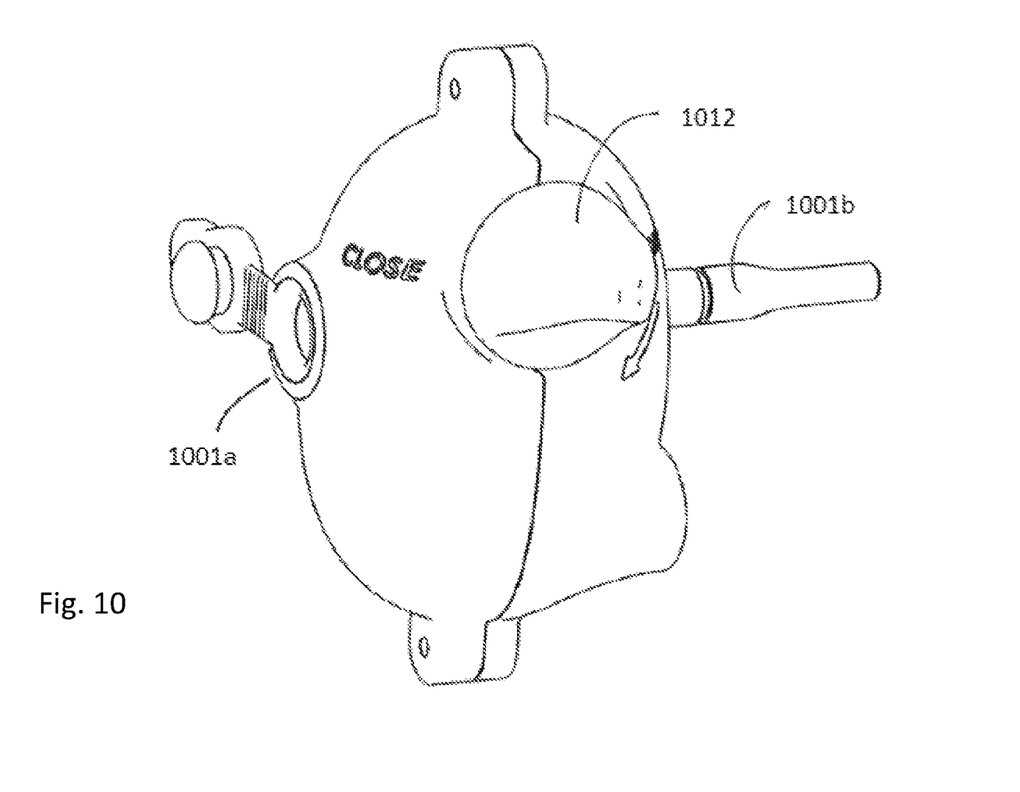
FIG. 10 is an external view of still another embodiment of the feeding device.

FIG. 10 is an external view of the new device. It includes an outer housing with an input port 1001a for the medical instrument and an output port 1001b intended to be inserted into the instrument channel of the endoscope system. The feeder device also includes a contact for the drive shaft, not shown in the figure, and a rotary button 1012 for operating the clutch. If needed, the button may of course be replaced with a lever.

Figure 11:
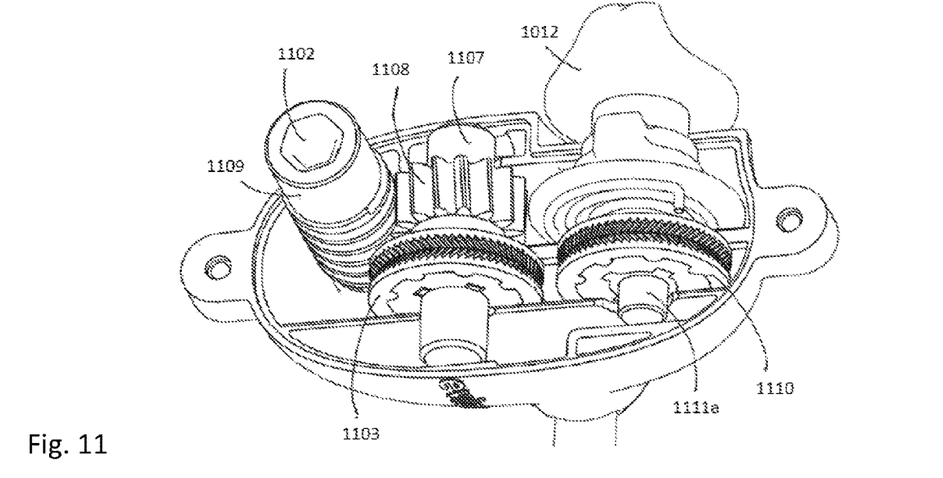
FIG. 11 is a perspective view of the innards of this embodiment.

FIG. 11 shows the interior of the feeding device. The drive mechanism includes a worm screw 1109 in mesh with gear cog wheel 1108. The worm screw includes a hexagonal socket 1102 for attaching to a drive motor. The cog wheel 1108 is connected to a shaft 1107 which drives the drive wheel 1103. Opposite the drive wheel 1103 there is an idler wheel 1110. The idler wheel is rotating freely on a spindle 1111. The spindle may be operated by the rotary button 1012 to shift the idler wheel towards the drive wheel for engaging a medical device passing between said wheels, thus acting as a clutch.

Figure 12:
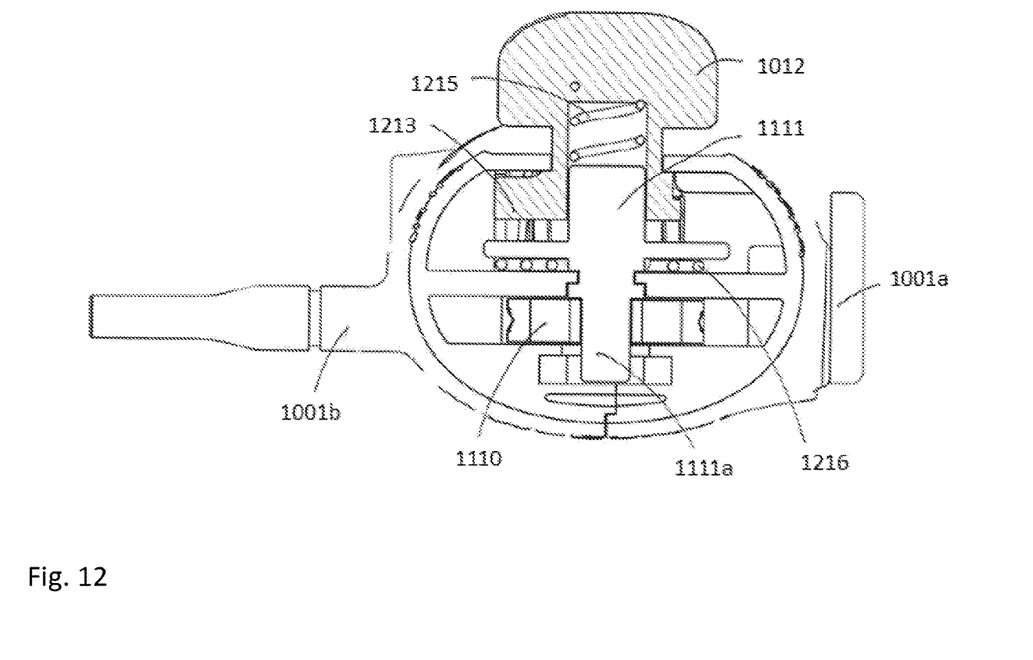
FIG. 12 is a sectional view of the embodiment shown in FIG. 6.

FIG. 12 is a sectional view through the feeding device showing the arrangement of the clutch mechanism. The rotary button 1012 includes a hollow stem 1214 in engagement with the spindle 1111. The button may slide up and down on the spindle against a first spring 1215 that forces the button upwards. The button is adapted to turn the spindle through a number of notches 1417 (FIG. 14) engaging corresponding ribs on the spindle. The button includes a rounded knob 1213 which when turned will slide against a tapered projection in the upper part of the housing forcing the button 1012 and stem 1214 downwards against the force of the spring 1215. When the button has been turned fully clockwise, the knob 1213 will pass over an edge of the tapered projection and snap back. Thus, it will be trapped by the projection preventing it from returning unless the button is depressed again allowing the knob to pass back over the edge. This holding mechanism is shown in greater detail in FIG. 15. The spindle 1111 is turned by the button 1012 against the force of a flat spring 1216, the spring being in engagement with the spindle.

Figure 13:
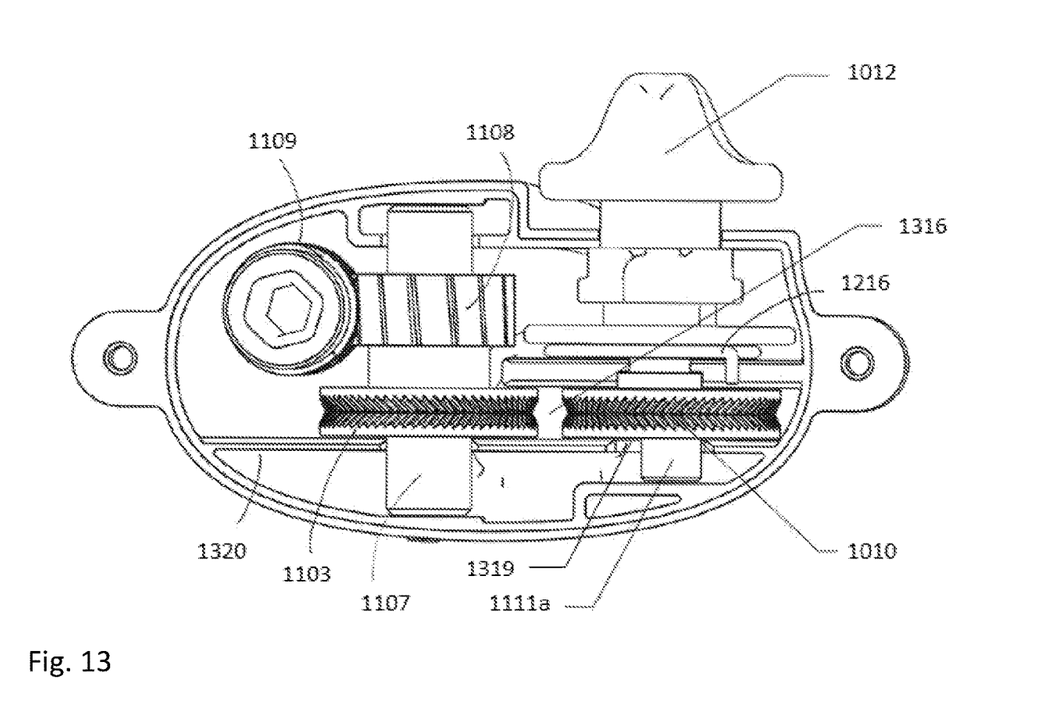
FIG. 13 is another sectional view of this embodiment, normal to the view of FIG. 7.

FIG. 13 is a corresponding section through the feeding device, this section being normal to the section shown in FIG. 12. Between the driven wheel 1103 and the idler wheel 1010 there is a space 1316 in line with the inlet gate 1001a and outlet gate 1001b wherein the medical instrument will pass. Note that the lower part 1111a of the spindle 1111 is eccentric, i.e. mounted offset from the center line of the main part of the spindle and runs in an arcuate recess or cutout 1319 in a wall 1320 traversing the housing of the device.

Figure 14:
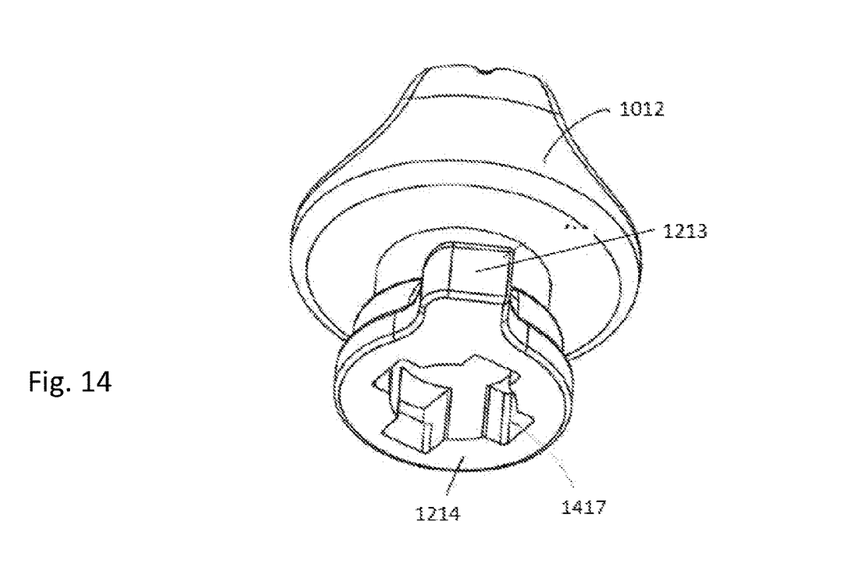
FIG. 14 is a perspective view of a component used in this embodiment.

FIG. 14 shows the rotary button 1012 in detail. In the hollow stem 1214 there are a number of notches 1417. The stem also includes a rounded knob 1213.

Figure 15:
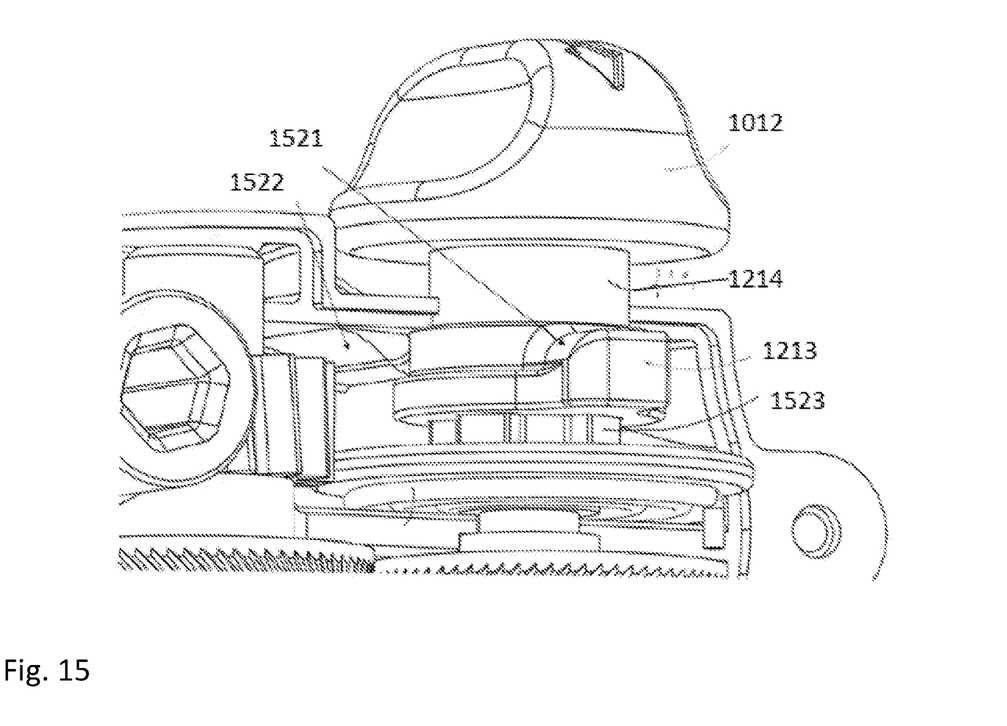
FIG. 15 is a perspective view showing how the component of FIG. 14 is installed in the inventive feeding device.

FIG. 15 shows the rotary button installed in the feeding device. The knob 1213 has a rounded part 1521 that is adapted to slide against the tapered projection 1522 on the inside of the housing. The figure also shows the ribs 1523 on the spindle 1111 which engage the corresponding notches 1417 (FIG. 14) in the stem part 1214 of the rotary button 1012.

In all other respects the embodiment of the feeding device shown in FIGS. 10-15 is designed in the same way as the first embodiment shown in FIGS. 2-5. Among other this relates to the design of the drive and idler wheels and how the device is operated. Further, a cassette solution as shown in FIG. 6-9 may also be included in this embodiment. While the embodiment shown in FIGS. 10-15 includes only one drive wheel with associated idler wheel, other versions with two or even more pairs of drive wheels and idler wheels may be realized.

The invention claimed is:

1. An instrument feeder device for use in an endoscope system, for feeding a medical instrument into a body or withdrawing the medical instrument from the body, the instrument feeding device comprising:
  a connector for connecting the instrument feeding device to a motor for moving the medical instrument through the instrument feeding device;
  a drive wheel arranged to be rotated by the motor, wherein the drive wheel is positioned on one side of the medical instrument;
  an idler wheel positioned on an opposite side of the medical instrument relative the drive wheel; and
  a clutch mechanism adapted to push the idler wheel against the medical instrument and thereby push the medical instrument against the drive wheel, hold the idler wheel in an activated position against the medical instrument, and release the idler wheel from said activated position, wherein the clutch mechanism includes a rotary button connected to a spindle, the spindle including a main part and an eccentric part which is arranged offset relative a center line through the main part, and wherein the idler wheel is rotatably mounted on said eccentric part of the spindle, wherein the rotary button includes a stem which is hollow and slidably mounted onto the main part of the spindle, the stem including notches engaging corresponding ribs on the main part of the spindle allowing the rotary button to turn the spindle, a knob on said stem engaging a tapered wedge on a wall encompassing the device, and a spring forcing the knob against the wedge.

2. The instrument feeding device according to claim 1, wherein the tapered wedge includes an edge on a far end thereof, said edge will hold the knob when passing over the edge.

\* \* \* \* \*